United States Patent [19]
Bayers

[11] Patent Number: 5,843,187
[45] Date of Patent: Dec. 1, 1998

[54] INSERTABLE INTRAOCULAR LENS

[76] Inventor: Jon H. Bayers, 1441 Liberty St., Ste. 205, Redding, Calif. 96001

[21] Appl. No.: 910,490

[22] Filed: Aug. 6, 1997

[51] Int. Cl.$^6$ ....................................................... A61F 2/16
[52] U.S. Cl. .................................................................. 623/6
[58] Field of Search .................................................... 623/6

[56] References Cited

U.S. PATENT DOCUMENTS

| | | | |
|---|---|---|---|
| 4,585,454 | 4/1986 | Fabricant | 623/6 |
| 4,624,670 | 11/1986 | Bechert, II | 623/6 |
| 4,666,445 | 5/1987 | Tillay | 623/6 |
| 4,781,717 | 11/1988 | Grendahl | 623/6 |
| 5,013,322 | 5/1991 | Rosa | 623/6 |
| 5,203,790 | 4/1993 | McDonald | 623/6 |
| 5,522,890 | 6/1996 | Nakajima et al. | 623/6 |

*Primary Examiner*—Randy C. Shay
*Attorney, Agent, or Firm*—Theodore J. Bielen, Jr.

[57] ABSTRACT

An intraocular lens, capable of being manipulated by a pulling tool through an limbal incision in the eye, which utilizes a optical portion. The optical portion takes the form of a flexible transparent body. A fixation element is also employed in the present invention for positioning the lens in a interior segment of the eye. The fixation means may consist of at least one appendage which is connected to the optical portion. The optical portion further possesses an engagement zone for permitting the exertion of a force adjacent the optical portion by a pulling tool. The integrity of the optical portion and/or the fixation element is maintained by reinforcement or strengthening of the same against forces exerted by the pulling tool.

7 Claims, 3 Drawing Sheets

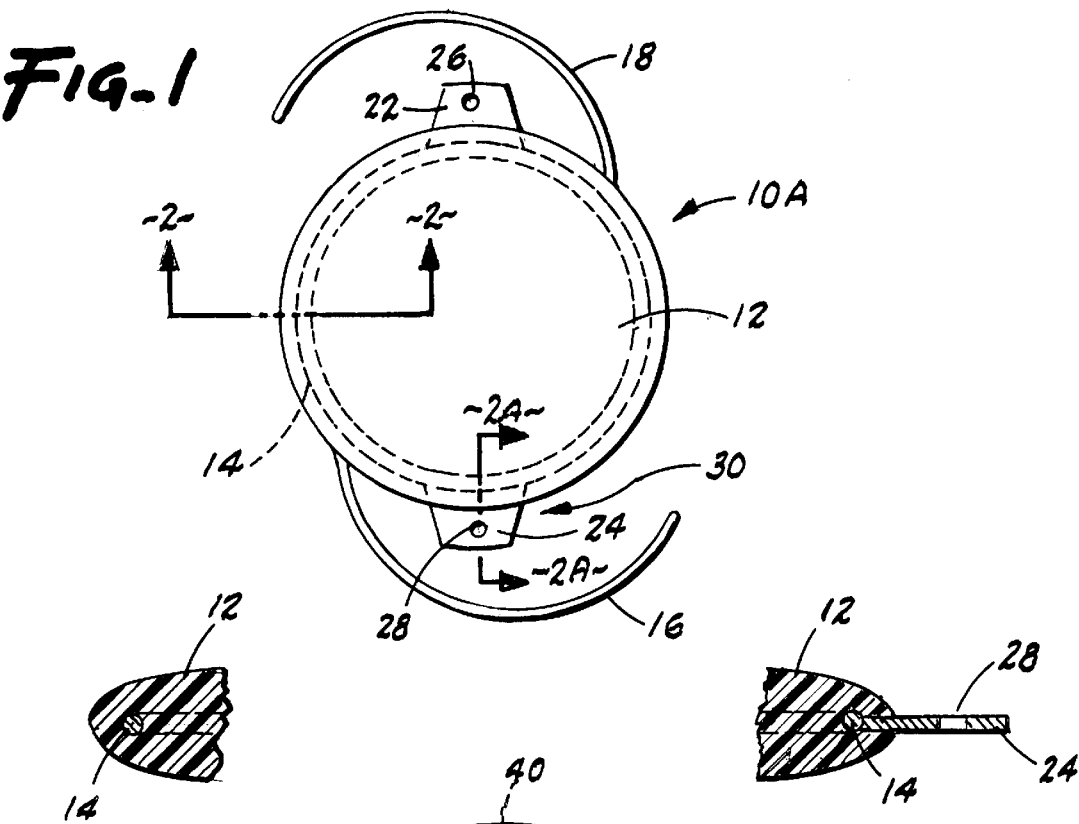
FIG-1
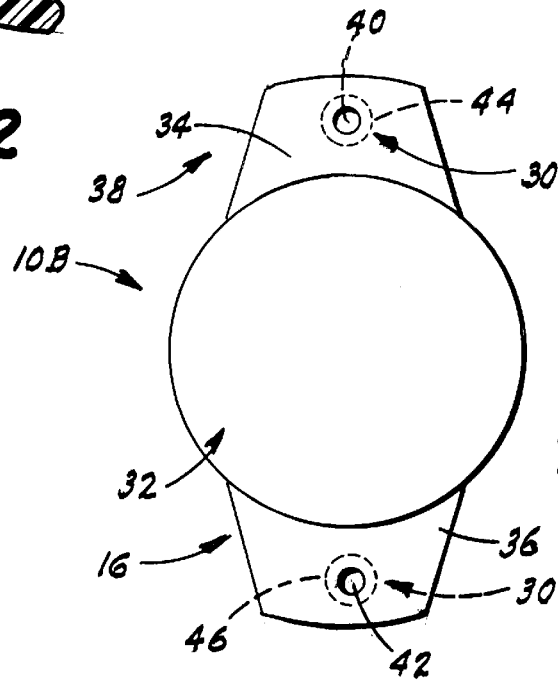
FIG-2
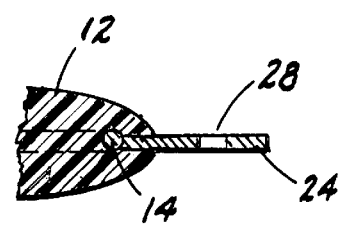
FIG-2A
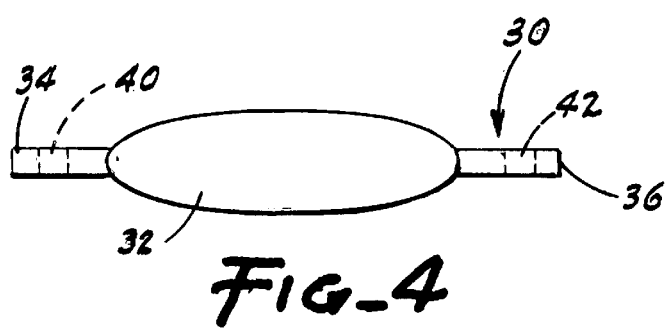
FIG-3
FIG-4

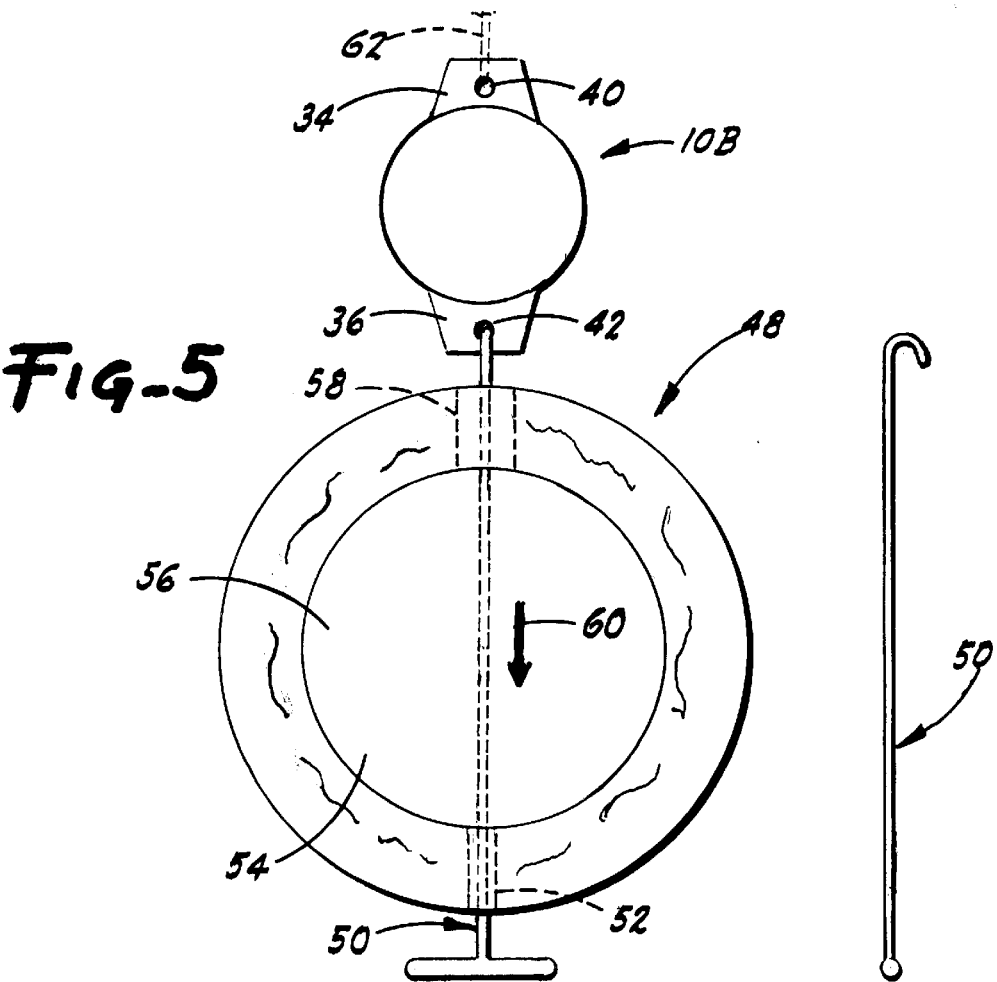
FIG-5
FIG-6
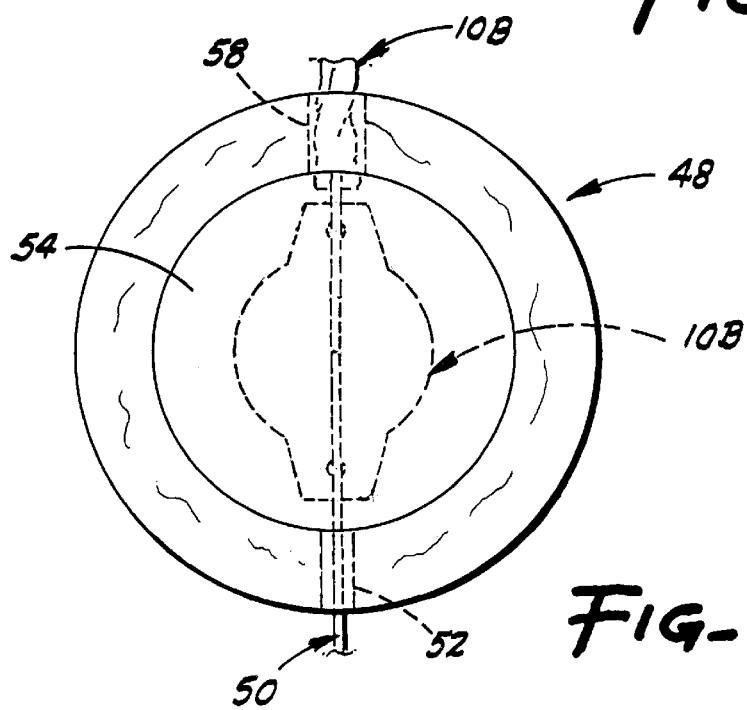
FIG-7

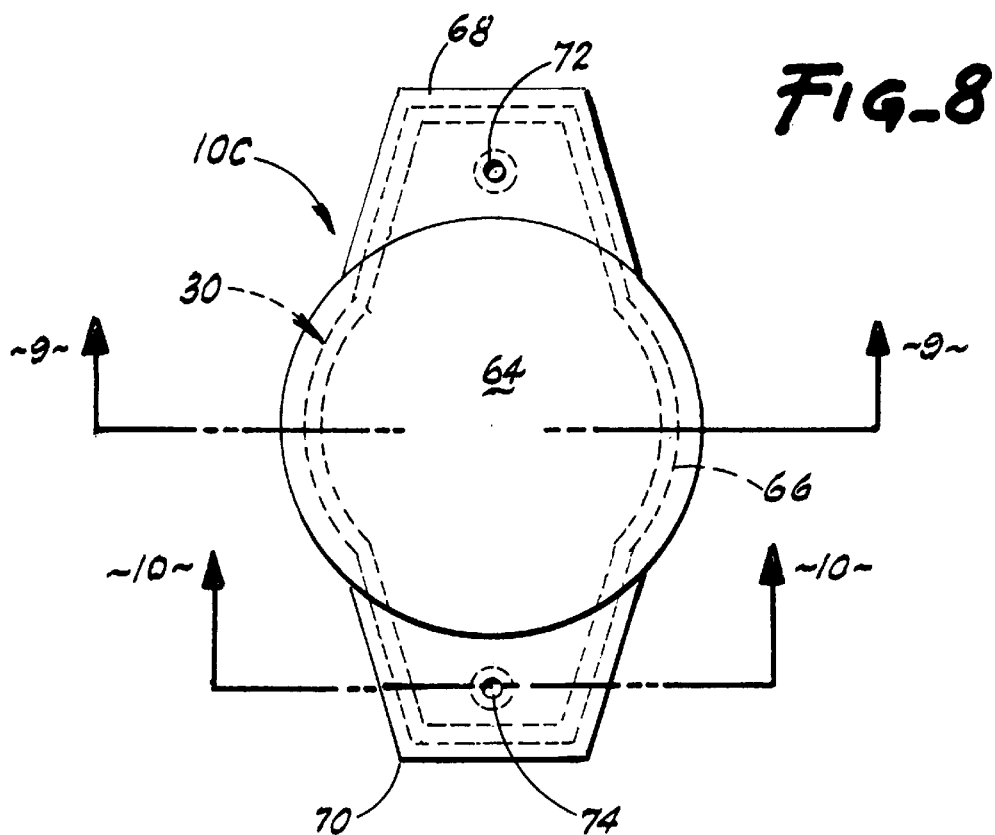
FIG_8
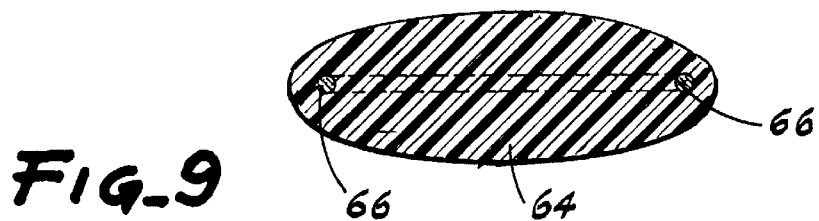
FIG_9
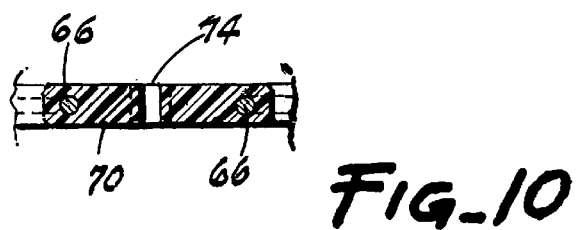
FIG_10

INSERTABLE INTRAOCULAR LENS

BACKGROUND OF THE INVENTION

Intraocular lenses have been used for many years to correct a cataract condition. The preferable place for insertion of an intraocular lens is in the posterior chamber following the removal of a portion of the natural lens.

A recent development concerns the use of intraocular lenses that are extremely flexible permitting them to be folded or rolled prior to insertion in the eye. Although a smaller incision permits the use of such lenses, specialized insertion devices such as folding or rolling instruments must be employed with these lenses. Thus, although the lens itself is capable of fitting through a small incision, the use of such insertion devices increases the ultimate size of the incision needed to place the intraocular lens within the eye.

An intraocular lens which is capable of fitting in a small incision without the use of an insertion tool would be a notable advance in the medical field.

SUMMARY OF THE INVENTION

In accordance with the present invention a novel and useful intraocular lens capable of being inserted through a small incision in the eye to correct a cataract condition is herein provided.

The intraocular lens of the present invention is capable of being manipulated by a pulling tool through a very small incision in the eye. The structure of the lens includes an optical portion which is a flexible transparent body capable of correcting the vision of the patient. For example, the optical portion may be formed of silicone or other biologically compatible material.

Fixation means is also employed for positioning the lens in a chamber of the eye. Such fixation means may take the form of a plate, or an appendage in an open or closed loop format. Appendages of this type also possess elasticity or springiness to permit the optical portion of the lens to remain in place in either the anterior or posterior chamber of the eye.

The lens of the present invention is also provided with an engagement zone for permitting the exertion of a pulling force on the optical portion and/or fixation means by the pulling tool for insertion into the eye. The pulling tool may take the form of a micro-hook or similar device. Such engagement zone may be constructed in the form of an aperture through a portion of the lens optical portion or a portion of the fixation means attached to the optical portion. In certain cases, the engagement zone may comprise an aperture which is formed on an auxiliary appendage connected to either of these elements of the intraocular lens. For example, a flange or plurality of flanges may be attached to the optical portion of the intraocular lens, each flange including an aperture for permitting engagement by the pulling tool. In addition, the engagement zone may be found as an aperture formed through a plate or haptic, which is normally used for fixation of the optical portion of the lens in the posterior chamber of the eye.

Strengthening means is also found in the present invention for selectively reinforcing the integrity of the optical portion of the lens or the fixation means i.e. to prevent tearing. Such strengthening means may take the form of a reinforcing flange, connected to the optical portion, a reinforcing band of material, formation of a area in the optical means or fixation means of a material which is stronger or thicker than the normal optical material used in the lens, or the like. For example, encircling or embedded elements are used to reinforce the lens. Such elements may circle the entire lens or an appropriate portion.

In certain cases, it may be practical to pull the lens of the present invention in two directions when being inserted into the eye. In such an instance, the lens may be formed with a pair of flanges each having an aperture to form the engagement zone and strengthening means permitting the application of such a pulling force. These flanges may take the form of plate attached to the optical portion of the lens or in the form of apertures through the existing haptics. In the latter case, such apertures may be reinforced or strengthened by bushings or other similar structures above.

It may be apparent that a novel and useful intraocular lens has been described.

It is therefore an object of the present invention to provide an intraocular lens which is capable of being manipulated by a pulling tool through a small incision in the eye during cataract surgery.

Another object of the present invention is to provide an intraocular lens capable of being manipulated by a pulling tool through an incision in the eye which is durable such that the pulling force exerted on such lens does not damage the lens during the process of insertion.

Yet another object of the present invention is to provide an intraocular lens that is capable of being manipulated for insertion or removal by a pulling tool through a minimal incision in the eye.

Yet another object of the present invention is to provide an intraocular lens capable of being manipulated by a pulling tool through an incision in the eye that eliminates the need for bulky insertion tools found in the prior art.

Another object of the present invention is to reduce trauma to an eye during insertion or removal of an intraocular lens.

The invention possesses other objects and advantages especially as concerns particular characteristics and features thereof which will become apparent as the specification continues.

BRIEF DESCRIPTION OF THE DRAWINGS

FIG. 1 is a top plan view of a first embodiment of the present invention.

FIG. 2 is a sectional view taken along line 2—2 of FIG. 1.

FIG. 2A is a sectional view taken along line 2A—2A of FIG. 1.

FIG. 3 is a top plan view of another embodiment of the present invention.

FIG. 4 is a side elevational view of the embodiment depicted in FIG. 3.

FIG. 5 is a top plan view illustrating the insertion of the lens of FIG. 3 into an eye.

FIG. 6 is a side elevational view of a portion of a micro-hook used to manipulate the intraocular lens depicted in FIG. 4.

FIG. 7 is a top plan view of the insertion of the lens of FIG. 3 to an eye where the lens is half-way through the incision and in place, the latter shown in phantom.

FIG. 8 is a top plan view of another embodiment of the present invention.

FIG. 9 is a sectional view taken along line 9—9 of FIG. 8.

FIG. 10 is a sectional view taken along line 10—10 of FIG. 8

DETAILED DESCRIPTION OF THE PREFERRED EMBODIMENTS

Various aspects of the present invention will evolve from the following detailed description of the preferred embodiments thereof which should be taken in conjunction with the prior described drawings.

The invention as a whole is shown in the drawings by reference character 10, with specific embodiments noted by the addition of upper case letters. The intraocular lens 10 includes as one of its elements an optical portion 12 which may be formed of any optical flexible material such as silicone. In this regard, optical portion 12 is foldable or capable of being rolled into a small configuration. The embodiment 10A of FIG. 1 shows optical portion 12 being surrounded by a circular band of material 14, such as nylon, which is stronger than the silicone material of the optical portion 12. Lens 10A includes fixation means 16 which is shown as springy arms 18 and 20. That is to say, arms 18 and 20 hold lens 10A in place in the posterior chamber of an eye after removal of a portion of the natural lens of the eye during cataract surgery.

Lens 10A also is provided with an engagement zone in the form of flanges 22 and 24. Flanges 22 and 24 each include an aperture 26 and 28, respectively. Apertures 26 and 28 are intended to serve as a place for engagement of a micro-hook or other pulling tool used in inserting lens 10A within an eye, which will be discussed hereinafter. Strengthening means 30 is also provided in lens 10A in the present invention, FIG. 1. Strengthening means 30 may take the form of band 14 being connected to flanges 22 and 24, or the formation of flanges 22 and 24 of a stronger material than the silicone, generally used to construct optical portion 12, FIGS. 2 and 2A.

Turning to FIGS. 3 and 4, it may be observed that another embodiment 10B of the present invention is illustrated. Lens 10B possesses an optical portion 32 similar to that shown in FIG. 1, except band 14 is missing. Haptics 34 and 36 are used as the fixation means 16 in substitution for springy arm 16 of embodiment 10A of FIG. 1. Engagement zone 38 takes the form of apertures 40 and 42 which pass through haptics 34 and 36. With reference to FIG. 3, it may be observed that bushings 44 and 46 surround apertures 40 and 42, respectively to provide extra strength and serve as strengthening means 30. Bushings 44 and 46 are depicted in FIG. 3 in phantom. FIG. 4 depicts strengthening means in the thickening of haptics 34 and 36, compared to flanges 22 and 24 of FIG. 2A.

FIG. 8 illustrates embodiment 10C of the application in which an optical portion 64 is employed. Imbedded within optical portion 64 is a filament or band of material which is generally stronger than the material used to construct optical portion 64. For example, if optical portion 64 is constructed of silicone rubber, band 66 may be constructed from nylon, polyester, or other materials. Band 66 encircles optical portion 64 and is also shown as encircling haptics 68 and 70. In other words, band or filament 66 serves as strengthening means 30, hereinbefore described. It should be noted, that FIGS. 8 through 10 illustrate band 66 with optical portion being assumed to be a transparent body. Openings 72 and 74 again permit engagement by the user with hook 50 found on FIG. 6. Of course, bands 66 may simply encircle optical portion 64 and haptics 68 and 70 may be formed of thickened or stronger material than optical portion 64.

In operation, the user inserts lenses 10A 10B or 10C into an eye 48, shown with exemplary lens 10B in plan view in FIGS. 5 and 7. A typical micro-hook 50 is illustrated in FIG. 6 to exert a pulling force on lenses 10A, 10B, or 10C, of course, other tools may be employed in this regard to exert a pulling force. A small incision 52 (about 3 mm), shown in phantom in FIGS. 5 and 7, permits hook 50 to enter the interior 54 of eye 48. Pupil 56 has been dilated in the usual manner to permit exemplary lens 10B to be used in cataract surgery. Incision 58 has been also placed through eye for passage of exemplary intraocular lens 10B. Hook 50 is then placed through aperture 42 of haptic 36 and pulled according to directional arrow 60. Lenses 10A, 10B, and 10C may be prefolded or rolled to aid in the passage through incision 58 which is generally quite small, 2 to 3 mm. Another hook 62 may be employed with aperture 40 of haptic 34 to slim lens 10B by a certain degree through stretching. FIG. 7 shows lens 10B in a folded or rolled configuration passing through incision 58 into interior of eye 54. The phantom rendition of lens 10B in FIG. 7 indicates that lens 10B has been placed in the posterior chamber of eye 48. After lens 10B has been pulled into eye 48, hook 50 is removed through incision 52.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An intraocular lens capable of being manipulated by a pulling tool through an incision in the eye comprising:
   a. an optical portion, said optical portion comprising a flexible transparent body;
   b. fixation means for positioning said lens in a chamber of the eye, said fixation means comprising at least one appendage connected to said optical portion;
   c. an engagement zone for permitting the exertion of a pulling force on said optical portion by the pulling tool; and
   d. strengthening means for selectively reinforcing the integrity of said optical portion, said strengthening means comprising a flange attached to said optical portion, and said engagement zone comprising an aperture through said flange, said aperture at least partially surrounded by material of greater durability than said optical portion.

2. The lens of claim 1 in which said flange is constructed of a material stronger than the material of said optical portion.

3. The lens of claim 1 in which said flange is a first flange and wherein said lens further comprises a second flange, said second flange attached to said optical portion opposite said first flange, said engagement zone further comprising an aperture through said second flange, said second flange aperture surrounding by material of greater durability than said optical portion.

4. The lens of claim 1 in which said optical portion is foldable.

5. The lens of claim 4 in which said optical portion is stretchable.

6. The lens of claim 3 in which said optical portion is foldable.

7. The lens of claim 6 in which said optical portion is stretchable.

\* \* \* \* \*